(12) United States Patent
Gebauer et al.

(10) Patent No.: US 11,499,647 B2
(45) Date of Patent: Nov. 15, 2022

(54) REMOTELY ACTUATED VALVE FOR A BIOLOGICAL LIQUID TREATMENT SYSTEM

(71) Applicant: GE Healthcare Bio-Sciences AB, Uppsala (SE)

(72) Inventors: Klaus Heinrich Gebauer, Uppsala (SE); Stefan Sjolander, Uppsala (SE)

(73) Assignee: Cytiva Sweden AB, Uppsala (SE)

(*) Notice: Subject to any disclaimer, the term of this patent is extended or adjusted under 35 U.S.C. 154(b) by 113 days.

(21) Appl. No.: 16/708,030

(22) Filed: Dec. 9, 2019

(65) Prior Publication Data
US 2020/0232576 A1 Jul. 23, 2020

Related U.S. Application Data

(63) Continuation of application No. 15/103,230, filed as application No. PCT/US2014/071405 on Dec. 19, 2014, now Pat. No. 10,533,680.
(Continued)

(51) Int. Cl.
*F16K 31/12* (2006.01)
*F16K 7/12* (2006.01)
(Continued)

(52) U.S. Cl.
CPC ............. *F16K 31/12* (2013.01); *B01D 15/10* (2013.01); *B01D 29/90* (2013.01); *C12M 29/00* (2013.01);
(Continued)

(58) Field of Classification Search
CPC ........... Y10T 137/0318; F16K 37/0041; F16K 31/12; F16K 7/12; B01L 3/502784;
(Continued)

(56) References Cited

U.S. PATENT DOCUMENTS 2,447,185 A  8/1948 Keim
4,304,257 A  12/1981 Webster
(Continued)

FOREIGN PATENT DOCUMENTS

CN  1155847 A  7/1997
CN  103007381 A  4/2013
(Continued)

OTHER PUBLICATIONS

International Search Report and Written Opinion regarding International Application PCT/IS2014/071405, dated May 15, 2015, 9 pages.
(Continued)

*Primary Examiner* — Peter J Macchiarolo
*Assistant Examiner* — Mohammed E Keramet-Amircolai
(74) *Attorney, Agent, or Firm* — Eversheds Sutherland (US) LLP

(57) ABSTRACT

The invention relates to valve system for controlling a process fluid within a liquid processing system. The valve system comprises a valve arrangement, a pneumatic control system, and a connector unit. When the valve arrangement is connected to the connector unit, two or more valves are formed, such that the pneumatic control system controls an open/close or pressure control mode of the valves. A pump diaphragm system is disclosed, as well as a system for purifying a biological material that comprises the valve system or the pump diaphragm system. Also discloses are methods of using the valve system or the pump diaphragm system in a process for the purification of a biological material.

17 Claims, 8 Drawing Sheets

Related U.S. Application Data

(60) Provisional application No. 61/918,393, filed on Dec. 19, 2013.

(51) Int. Cl.
 *B01D 15/10* (2006.01)
 *B01D 29/90* (2006.01)
 *C12M 1/00* (2006.01)
 *C12M 1/34* (2006.01)

(52) U.S. Cl.
 CPC ............ *C12M 41/40* (2013.01); *C12M 47/12* (2013.01); *F16K 7/12* (2013.01); *B01D 2201/16* (2013.01); *B01D 2201/202* (2013.01)

(58) Field of Classification Search
 CPC . C08L 79/02; E03B 9/14; C12M 1/00; C12M 1/34; B01D 29/90; B01D 15/10
 USPC .............................................. 137/1; 73/61.56
 See application file for complete search history.

(56) References Cited

U.S. PATENT DOCUMENTS

| | | | |
|---|---|---|---|
| 4,848,722 A | 7/1989 | Webster | |
| 5,593,130 A * | 1/1997 | Hansson | F16K 7/126 251/359 |
| 6,270,326 B1 | 8/2001 | Kuriyama | |
| 6,712,963 B2 | 3/2004 | Schick | |
| 8,308,698 B2 | 11/2012 | Wagner | |
| 10,451,591 B1 * | 10/2019 | Gebauer | F16K 99/0015 |
| 2002/0100449 A1 * | 8/2002 | Gebauer | F01L 1/32 123/188.9 |
| 2002/0128593 A1 * | 9/2002 | Sjolander | G01N 35/1097 604/22 |
| 2003/0017059 A1 * | 1/2003 | Loy | F04B 27/1804 417/213 |
| 2008/0077068 A1 * | 3/2008 | Orr | F04B 53/109 604/6.11 |
| 2008/0078462 A1 * | 4/2008 | Minervini | F16K 31/12 137/625.64 |
| 2008/0115599 A1 * | 5/2008 | Masters | B01L 3/502715 73/866 |
| 2009/0120503 A1 * | 5/2009 | Donahue | F16K 17/14 137/1 |
| 2010/0043891 A1 * | 2/2010 | Wilke | F16J 15/3236 137/484.2 |
| 2010/0069830 A1 * | 3/2010 | Grigorov | A61M 5/16881 604/67 |
| 2010/0108920 A1 * | 5/2010 | Tatarek | F16K 7/12 251/61 |
| 2010/0139779 A1 * | 6/2010 | Lautzenheiser | E03C 1/04 137/511 |
| 2010/0264265 A1 | 10/2010 | Evans | |
| 2010/0269918 A1 | 10/2010 | Rudolph | |
| 2010/0274128 A1 * | 10/2010 | Wagner | A61M 5/1454 600/432 |
| 2011/0132838 A1 * | 6/2011 | Curtis | A61M 1/1601 210/637 |
| 2011/0155068 A1 * | 6/2011 | Maier | A01J 7/02 119/14.18 |
| 2012/0006736 A1 * | 1/2012 | Cirou | B01D 61/30 210/232 |
| 2012/0149885 A1 * | 6/2012 | Niazi | B01F 27/9212 530/413 |
| 2012/0292236 A1 * | 11/2012 | Jacobs | B01D 37/025 210/96.1 |
| 2013/0064738 A1 * | 3/2013 | Berger | B01J 4/008 422/521 |
| 2014/0138564 A1 | 1/2014 | Moeller | |
| 2014/0007660 A1 | 5/2014 | Adams | |

FOREIGN PATENT DOCUMENTS

| | | |
|---|---|---|
| JP | 2011157381 A | 6/1999 |
| JP | 2006112562 A | 4/2006 |
| JP | 2009519440 A | 5/2009 |
| JP | 2010535339 A | 11/2010 |
| JP | 2010536484 A | 12/2010 |
| WO | 2009026060 A2 | 2/2009 |

OTHER PUBLICATIONS

Chinese Office action for Chinese Patent Application 201480069304, Serial No. 2018022302087330, dated Feb. 27, 2018, 11 pages.
Japanese Notice of Allowance for JP Application No. 2016-540629, dated Mar. 26, 2019, 4 pages.

* cited by examiner

REMOTELY ACTUATED VALVE FOR A BIOLOGICAL LIQUID TREATMENT SYSTEM

FIELD OF THE INVENTION

The present invention relates to the field of biopharmaceutical purification. More specifically, the present invention is directed to novel valves for use in a system for the treatment of biological liquids containing biopharmaceuticals, as well as method of using the same.

BACKGROUND OF THE INVENTION

Biopharmaceuticals have become an increasingly important part of modern medicine. The production of these biopharmaceutical drugs poses unique challenges. These products are in general obtained by culturing a host cell in a bioreactor to produce the drug substance of interest, followed by a number of liquid treatment steps such as clarification of the cell culture, filtration and chromatography steps. Effective liquid handling thus is a major requirement for any system that processes these products. Many workflows are also required to be run under controlled and contained conditions, which may involve aseptic handling in closed fluid handling systems and the use of pre-sterilized components, which is another major requirement for such systems.

Recently, automated biological liquid handling systems based on single-use flow paths have become available on the market. Single use flow path components offer the advantage that time- and labor consuming pre- and post-use cleaning of the wetted flow path is eliminated, thus increasing overall process efficiency and thereby reducing cost. The elimination of equipment cleaning and associated cleaning validation also greatly reduces the risk for cross-contamination in between different campaigns and drug substances, thus increasing overall process and drug safety. As the single-use components are utilized as consumables that are to be disposed after a process run or campaign, a design of systems and consumables to achieve overall cost efficiency and flexibility is a key interest to suppliers, users in the biopharma industry and eventually patient care. Flexibility is required to adapt the system and its single-use components to the liquid processing task of interest, such as for example chromatography, filtration etc. Depending on the sample and the specific process regimes required, flexibility is also required with regard to specific configuration within a selected processing task. A chromatography separation task may for example involve a larger or smaller number of inlets, outlets and components required, such as sensors, pumps etc.

ÄKTA ready (GE Healthcare) is a single-use liquid chromatography system built for process scale-up and production for early clinical phases. The system is intended to be used with ready-to-use, disposable flow paths that are deployed as consumables and disposed of after processing. The system uses 18 re-usable pinch valves installed in a fixed pattern at the instrument to manage fluid control in an interchangeable, single-use fluid path assembly. Flexible tubing of the fluid path assembly is fitted to the re-usable pinch valves according to a fixed installation scheme. The tubing and flow path is removed after processing to allow for disposal and installation of a new flow path.

The ÄKTA ready system controls the pinch valves with a "pneumatic distributor" mounted inside the instrument, the pneumatic distributor comprising a common air inlet for pressurized air and a control valve arrangement distributing and regulating the air pressure towards the pinch valves for control of the process liquid at side of the consumable, the single use flow path. Each pneumatic pinch valve is connected via a pneumatic conduit to its respective control valve at the pneumatic distributor in a fixed configuration and layout.

Millipore's FlexReady chromatography system uses a "clamshell" design, which is a cassette comprising the consumable flow path, which is made up from a flexible bag with welded conduits forming the flow path. The clamshell also comprises required valving to open or close the fluid conduits of the disposable parts. Further, the clamshell comprises the "pneumatic distributor" that controls the pressurization of the fluid driven (pneumatic) valves controlling the flow of process liquid inside the conduits of the single-use consumable. The "pneumatic distributor" is again a control valve arrangement fed by a common pressurized air supply. The clamshell is interchangeable and different clamshells configured for different unit operations such as chromatography or filtration can be fitted to the instrument. In this regard, flexibility is provided to adapt to different liquid processing tasks by replacement of the clamshell. Each clamshell is however dedicated to a specific configuration of the consumable that is used for example for either chromatography or filtration. Therefore, the pneumatic controller in the clamshell will operate solely the specifically configured clamshell, other clamshells do require their own pneumatic distributor. Further, the pneumatic distributor in a given clamshell is configured to solely interact with and control the valve arrangement for a specific configuration of the single-use fluid flow path, the consumable. This design has also a need for multiple, fixed configured pneumatic distributors, which will impact overall cost of system hardware, complexity, as well as weight, size and ease of use for each clamshell. See WO2011154885 and US20130240065A1.

Pneumatically controlled valve arrangements have also been proposed for simulated moving bed chromatography. Examples of such valves are described in U.S. Pat. No. 7,846,335B2, U.S. Pat. No. 8,196,603B2 and U.S. Pat. No. 7,790,040B2.

US20110005984A1 proposed a two part valve. A separate, and potentially single-use valve part contacts the medium, and a reusable pneumatic actuator forms a separate part that is positioned adjacent to the valve part. The two parts may be connected to become a working valve. These valve arrangements are however bulky and inflexible as the seizing and positioning of the consumable parts and flow conduits adjacent to the latter cannot be selected independently from the size, position or configuration of the pneumatic actuator part.

While the fixed configurations in between valve manifolds and their pneumatic control systems described above is industry standard for single-use biological liquid processing systems, there are a number of disadvantages of fixed configurations with regard to limited flexibility, increased cost and a large physical size and weight involved in handling of the systems and its single-use consumables.

There is a need for better valve design that offers low cost and high flexibility for biological liquid handling, especially for the production of biopharmaceuticals.

SUMMARY OF THE INVENTION

Improved valve technology is crucial for the success of second generation automated single use systems for large scale biological liquid processing that provides performance, ease of use, cost efficiency and modular flexibility. Certain embodiments of the invention provide such an improved valve system. The system comprises a valve arrangement and a pneumatic control system which is reused by re-addressing it when interchanging different flow path consumables. The system also comprises a connector. This valve system is highly flexible, as the pneumatic control system may be adjusted to fit different flow paths for different processes, i.e., chromatography or filtration, or for different capacities and fluid flow range, respectively. Since only the valve arrangement is in contact with process liquid, the valve arrangement may be pre-sterilized as a single use unit. The valve arrangement may be made by injection molding, and thus reduce the cost of the valve system.

DETAILED DESCRIPTION OF THE PREFERRED EMBODIMENTS

Figure 1:
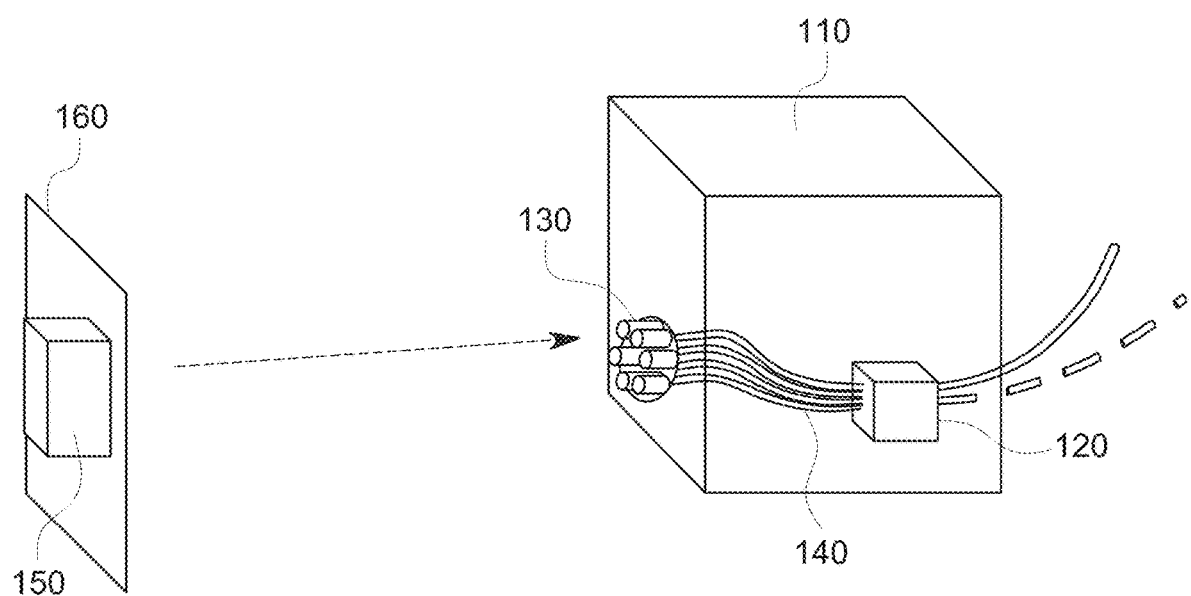
FIG. 1 presents a schematic of a remotely actuated, pneumatic valve system according to certain embodiments of the invention.

In one aspect, the invention provides a fluid control system for a biological liquid processing system.

Thus, in one embodiment, it is provided a valve system for controlling a process fluid within a liquid processing system, comprising
 a) a valve arrangement comprising (i) a wetted part comprising two or more inlet conduits, an outlet conduit, and a plurality of valve components capable of controlling the flow in the conduits; and (ii) a plurality of first actuators that control the flow in the conduits;
 b) a pneumatic control system comprising a plurality of second actuators, and a plurality of pneumatic conduits interconnecting the second actuators with the plurality of first actuators; and
 c) a connector unit for connecting and disconnecting at least two of the pneumatic conduits interconnecting the second actuators with the plurality of first actuators; wherein when the valve arrangement is connected to the connector unit, two or more valves are formed, such that the second actuator controls an open/close or pressure control mode of the valves.

The valve arrangement includes a plurality of valve components, one side of which is in direct fluid contact with a process fluid, these valve components, as part of the valve system, are capable of controlling the fluid flow of process fluid in a single-use flow path. Typical sizing of fluid path is between 1-32 mm in diameter, although smaller and larger flow path are also feasible.

The pneumatic control system controls the plurality of valves through controlling the fluid pressure (liquid or gas) to actuate the valve position of the valve arrangement in between fully open and fully closed as well as intermediate closing and opening positions, for example for accommodating the functions of ON/OFF valves and pressure control valves at side of the valve arrangement. Further, the pneumatic control system includes a plurality of pneumatic conduits for interconnection being inter-mediated by at least one connector unit, thus allowing for interchanging fluid lines and/or the configuration of fluid conduits at side of the valve arrangement. The pneumatic control system may comprise electromagnetic valves or motor driven valves to modulate the pneumatic pressure inside the pneumatic conduits connected to the valve arrangement.

The connector unit allows for the connection and disconnection of a plurality of pneumatic conduits in the pneumatic control system with the conduits of the valve arrangement.

In certain embodiments, the configuration or spatial arrangement of the valve arrangements or the connector unit may be altered to change the valve system's mode of operation.

In other embodiments, the configuration of the connector unit is altered to change the valve system's mode of operation.

In still other embodiments, the configuration of the pneumatic control system is altered to change the valve system's mode of operation.

Alteration of the configuration or spatial arrangement of the valve arrangement, the connector unit and the pneumatic control system may be achieved, for example, physically such as by re-location, re-positioning or re-orientation, electrical or electronically such as by rewiring or readdressing control elements, or through alternative fluid conduit arrangement. For example, the configuration of the pneumatic control system may be altered to re-addressing valves in the pneumatic control system or re-assigning valve positions matching for example an altered configuration of the valve arrangement.

The valve system has a low holdup volume and minimum back-mixing as compared to the standard valve arrangements used in traditional systems. Further, the valve arrangement may be a disposable part that is cost efficient and of low mechanical complexity, yet provide great flexibility in spatial positioning and configurability. Part of the configurability is achieved by re-positioning the fluid driven, second actuators inside the system cabinet, through a remote control of a valve via pneumatics or preferably by electrical or electronic control, for example by using electromagnets engaging the second actuators.

Thus, in certain embodiments, the plurality of second actuators and pneumatic conduits of the pneumatic control system are situated inside a cabinet hosting the liquid processing system, while the connector unit is situated on an external panel of the cabinet. While the pneumatic driven, second actuators could be placed at a remote location inside the cabinet of the biological liquid processing system, the pneumatic actuation of the first valves are driven via pneumatic conduit connections that provide spatial flexibility.

The valve arrangement as the only wetted part of the valve system may be a single use part, and is simply connected and secured to the pneumatic control system by a connector unit. The valve arrangement may also be pre-sterilized. In certain embodiments, the valve arrangement is provided as a closed and contained unit with aseptic/sterile connectors and/or dis-connectors that maintain the sterility or controlled environment of the internal flow path space during interconnecting or dis-connecting the flow path to other fluid processing or fluid transfer units without exposing the internal volume to the environment. In certain embodiments aseptic connectors such as the ReadyMate™ type connectors (GE Healthcare) may be used for connecting the flow path between the valve arrangement and the other fluid processing or fluid transfer units. Hereby, sterility can be maintained and operator safety is ensured by avoiding exposure of the environment by potentially harmful components treated in the fluid processing unit. The pneumatic control system is reusable and has no need for sterilization. The valve arrangement is preferably packaged in a form suitable for sterilization, for example by wrapping in one or multiple sealed bags and then sent for gamma irradiation.

In certain embodiments, the valve arrangement in the valve system is formed by two modules, the first module comprising the wetted part, the second module comprising the plurality of first actuators.

In certain embodiments, the first and second modules are secured by means of a clamping device or a clamping plate. Alternatively, the first and second modules may be secured by screws and bolts.

In certain embodiments, the first module of the valve arrangement is formed from a flexible pouch that is secured by a clamping device or a clamping plate.

A schematic of the remotely actuated, pneumatic valve system is presented in FIG. 1, with the valve arrangement (150) embodied as a valve block. The single-use flow path of a biological liquid processing system comprising the valve block resides preferable at the outside of a system cabinet (110), while the re-usable pneumatic valve system preferably resides at the inside of the system cabinet (110). The pneumatic control system comprising a plurality of pneumatic actuators (120) mounted inside the cabinet, a connector unit and pneumatic actuation chambers (130) situated preferably on an external panel of the cabinet, and a plurality of pneumatic conduits (140) connecting the pneumatic actuator (120) and each individual pneumatic channel and connection point of the connector unit (130).

The connector unit (130) and the valve arrangement (150) in or adjacent to the single-use flow path (160) together form valves. Depending on physical position of the valves at side of the single-use flow path, pneumatic conduits in between the connector unit and the valves of the single-use flow path are typically applied, and preferably integrated in the single-use flow path assembly.

Figure 2A:
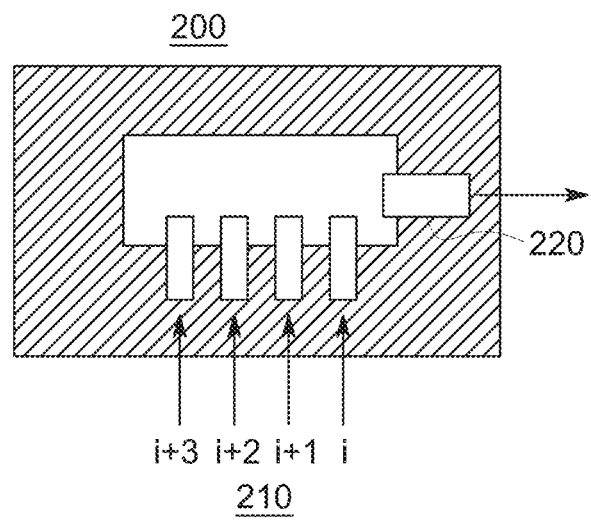
FIGS. 2A-2B present a schematic of a valve arrangement for the remotely actuated, pneumatic valve system according to certain embodiments of the invention, as well as a cross-sectional side view of such a diaphragm valve.
Figure 2B:
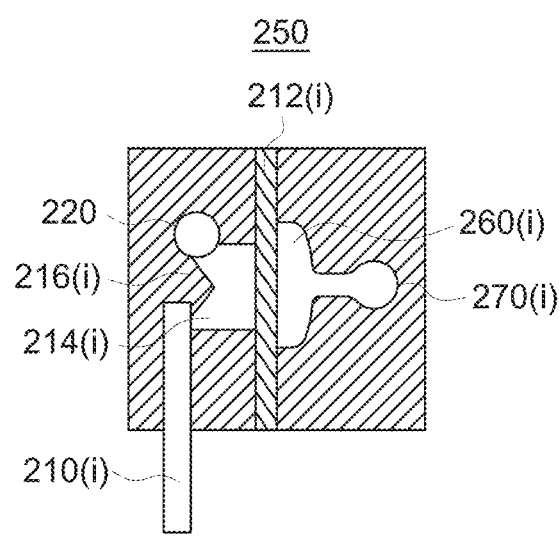

A representative valve arrangement (200) for the remotely actuated, pneumatic valve system is illustrated in FIG. 2A. FIG. 2B shows a cross-sectional side view of a representative diaphragm valve (250). The valve arrangement is comprised of two or more inlet conduits (four shown here) (210) for management of the biological fluid, an outlet conduit (220) and a corresponding number of diaphragms (212) covering the inlet conduits (210) to form individual valve positions. Each inlet conduit (210) includes a valve chamber (214) with a valve saddle (216), such that an opening between an inlet and an outlet may be controlled by the position of the diaphragm (212). While a diaphragm valve type is shown here, it is clear that many alternative configurations and designs for valves driven by pneumatic actuation exist, which fulfill the same requirements. Also, many different configurations for a flow path manifold do exist, where the flow of liquid needs to be controlled by valves. The drawings included in this document thus only serve as an illustration, and the invention is not limited to the design shown here. For example, while FIG. 2A shows a somewhat two dimensional arrangement of the valve arrangement in a single plane, three dimensional arrangements may be advantageous in certain situations. Thus, it is envisioned that the inlet and/or outlet conduits may locate at multiple sides/surfaces of the valve arrangement.

The valve arrangement is preferably built from injection molded parts for reduced cost. In some embodiments, the valve arrangement and the single-use flow path is preferably build from transparent or translucent material to allow visual observation of liquid and air displacement.

In the illustration shown (FIG. 2B), the valve arrangement (200) is designed with diaphragm valves (250) and classical saddle seats adjacent to the diaphragm (212). The valve diaphragm (212) is comprised of a polymer that is sufficiently pliant to permit deflection when pneumatic pressure is relieved. Such pliant pressure responsive material may be a fluoropolymer. In an exemplary embodiment, the valve diaphragm is formed of perfluoroalkoxy copolymer resin thermoplastic material having a width of 0.01 inches though other materials and thicknesses may be used. While the diaphragm valve (250) is preferable for reasons of simplicity, performance and scalability, other configurations for valves driven by pneumatic actuation may equally be feasible, for example a counter press valve, rocker valve etc.

When the valve arrangement and the connector unit are connected, a diaphragm valve is formed between an inlet conduit and an outlet conduit (collectively the valve chamber) at side of the single-use liquid flow path, and a pneumatic actuation chamber (260), with the diaphragm at side of the single-use liquid flow path separating the valve chamber and the pneumatic actuation chamber (FIG. 2B). Each pneumatic actuation chamber is connected to the pneumatic control system through a pneumatic conduit (270) and the connector unit.

For the example of the diaphragm valve, a spring loaded design at the valve arrangement facilitates a full stroke for a normally open or normally closed position. Alternatively, a vacuum pump controlled to moderate gauche pressure may equally retract the diaphragm for a 'fully open' position. This vacuum pump solution facilitates further cost reduction and reduced complexity at side of the disposable valve. In any event, when pneumatic pressure is applied, the diaphragm is urged against the valve saddle in the valve chamber in sealing engagement, and when pressure is released, it deflects due to pressure from the fluid flow.

In certain embodiments, valves may be designed with proportional control properties allowing the restriction of flow to achieve a desirable pressure upstream the valve. Such functionality is for example desired for the control of tangential flow filtration in order to control the transmembrane pressure over the filter by throttling the flow at the outlet of the filter. In order to achieve such functionality with the shown example of a diaphragm valve, the pneumatic control pressure would be adjusted by the pneumatic control system to equal an intermediate pressure level that is lower than the pneumatic pressure applied for full fluid tight closure of the valve yet higher than the lowest pressure applied for fully opening the valve.

In certain embodiments, instead of the diaphragm shown in FIG. 2B, means of a mechanical component assumes the actuator function, the mechanical actuator being engaged by a pneumatic system. In certain embodiments, the mechanical actuator being engaged by a pneumatic system may interact with a component at the single-use valve arrangement that alters position or shape in order to open, close or regulate the liquid flow in the internal of the single-use flow path, such as a diaphragm, flap, lever etc.

In certain embodiments, the pneumatic control system, the connector and conduits for actuating the single-use valve may be designed as liquid driven, hydraulic, system, too.

The novel valve system according to certain embodiments of the invention offers unique design flexibility for a biological liquid processing system. For example, the configuration or spatial arrangement of the valve arrangements and the connector unit may be altered to change the valve system's mode of operation.

Different valve arrangements may be connected to a standard connector unit. Thus, in certain embodiments, the valve arrangement and the connector unit each contain one or more positioning features to ensure that they are properly aligned when connected. The control of the valve arrangement is configured by system software and the supervision of the pneumatic control system inside the cabinet. Any number of variations is possible for connecting a range of simpler to more complex valve configurations. Such variations may be required to adapt the system in a modular fashion to different sizes and system capacities as well as to different unit operations and flow path versions, such as chromatography, filtration etc.

Figure 3B:
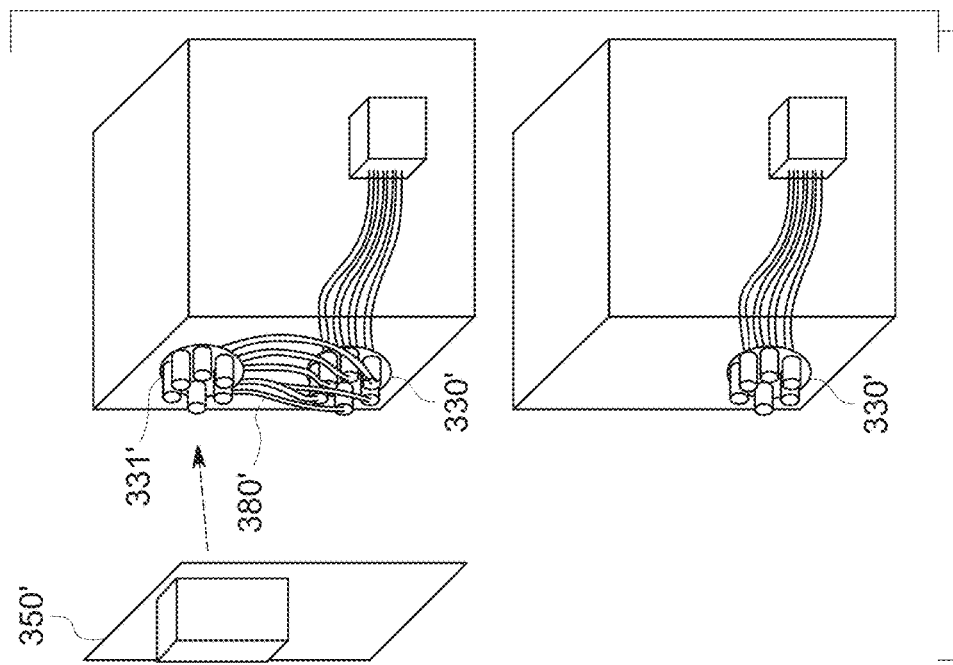
FIGS. 3A-3C present schematics of alternative designs of the valve system according to certain embodiments of the invention.
Figure 3A:
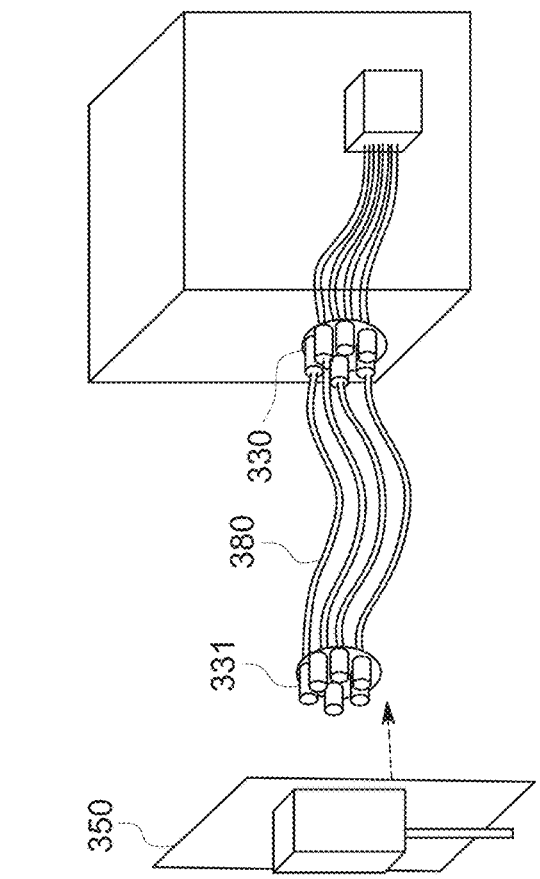
Figure 3C:
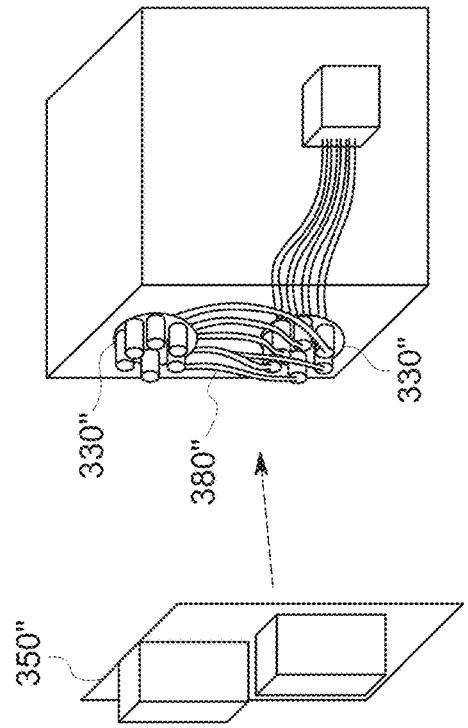

FIGS. 3A-3C present three exemplary flexible, alternative designs of the valve system. In a first example, when the valve arrangement (350) needs to be positioned away from the connector unit (330) on the external panel of the biological liquid processing system, a pneumatic extension harness (380) may be employed to connect the connector unit (330) and the valve arrangement (350). The extension harness (380) acts as an extension of the pneumatic control system, with the same number of fluid conduits as the pneumatic control system. One end of the extension harness (380) connects with the connector unit (330), thus each of the fluid conduits from the extension harness forms a continuous conduit with a corresponding pneumatic conduit of the pneumatic control system. The other end of the extension harness acts as a connector unit (331), when connected with the valve arrangement, a valve is formed.

In a second example, when the valve arrangement (350') needs to be positioned at a different position on the external panel of the biological liquid processing system from the connector unit (330'), a lateral extension harness (380') may be employed. Similar to the first example, the extension harness (380') acts as an extension of the pneumatic control system, with the same number of pneumatic conduits as the pneumatic control system. One end of the extension harness (380') connects with the connector unit (330'), thus each of the fluid conduits from the extension harness forms a continuous conduit with a corresponding pneumatic conduit of the pneumatic control system. The other end of the extension harness (331') acts as a connector unit, when connected with the valve arrangement (350'), a valve is formed. One advantage of using an external lateral extension harness may be that an external harness can replace corresponding pneumatic conduits in the otherwise integrated single-use consumable, hereby allowing cost reductions, a more compact design of the single-use consumable or other advantages in enhanced functionality, improved ease of use or reduced design complexity. Preferably, the lateral extension harness would be integrated in an intermediate layer or plate positioned in between the system cabinet with its pneumatic control system and the single-use flow path.

In a third example, a specially configured lateral extension harness (380") may be employed to enable different valve configurations by using and connecting only to a subset of pneumatic connections at the pneumatic connector. Another subset of pneumatic connection at the pneumatic connector unit can be connected to a different configuration without or with a different pneumatic harness. Thus, lateral extension harness (380") with particularly configured connector unit (330") on one end may be mounted to the external panel of the biological liquid processing system, with the other end of the harness connected to the connector unit (380") of the pneumatic control system. These particularly configured connector unit (380"), when used with correspondingly designed valve arrangements (350"), provide specifically configured valves for unique applications, e.g., chromatography, filtration etc.

In certain embodiments, multiple pneumatic connector units may be used to interface to the single-use flow path. These multiple pneumatic connectors may be addressed individually; however, parallel configurations of pneumatic lines may be employed, too.

In certain embodiments, the pneumatic actuator interface module may be directly mounted to connector and instrument cabinet (Figure not shown).

Figure 4:
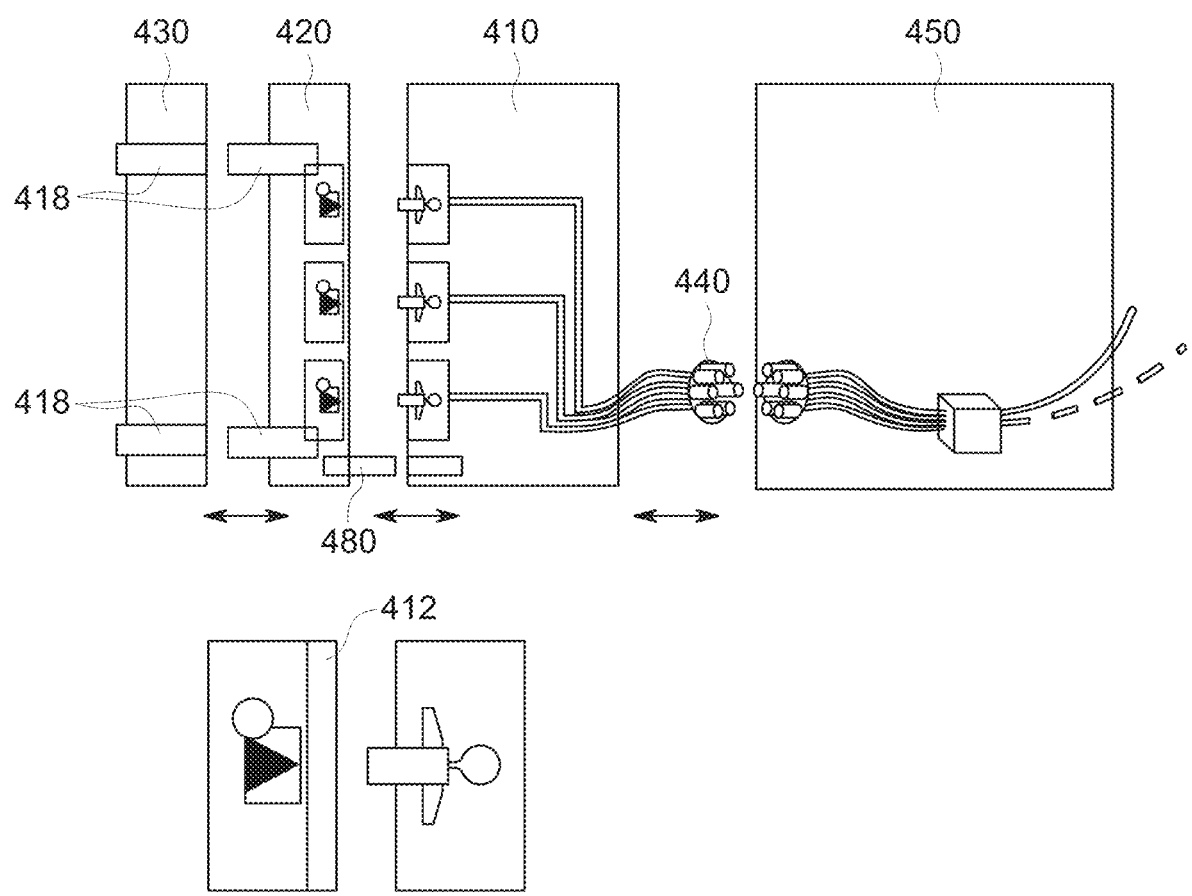
FIG. 4 shows a schematic of a variation of a remotely actuated, pneumatic valve system according to certain embodiments of the invention.

In certain embodiments, the valve system further includes a clamping plate (430) to mount and secure the valve arrangement against the system cabinet (450) and/or the pneumatic connector unit (440). The clamping plate (430) may preferably also mount and secure other components of the single-use flow path such as a pump unit against a pump drive, a sensor unit against a sensor reader or transmitter part and so forth. In certain embodiments, the valve arrangement may be formed by two modules, the first module comprising the wetted part, the second module comprising the plurality of first actuators. Further, the clamping plate (430) may be used to mount and secure the single-use wetted part (fluidic device (420)) against the pneumatic actuator interface module (410) including the plurality of first actuators (FIG. 4). Further, the clamping plate (430) may be used to mount and secure at least one of the layers of single-use wetted part (fluidic device (420)), pneumatic actuator interface module (410) including the plurality of first actuators, pneumatic connector unit (440) and system cabinet (450) against each other (FIG. 4). The pneumatic actuator interface module (410) is configured to match the configuration of the single-use fluidic device (420), and may be positioned adjacent to the fluidic device (420), the clamping plate (430) mounting and securing the single-use fluidic device (420) against the pneumatic actuator interface module (410). The valve arrangement at side of the single-use fluidic device (420) is situated substantially at the interface between the fluidic device (420) and the pneumatic actuator interface module (410), allowing interaction between movable actuators (might be a piston) in the pneumatic actuator interface module (410) and diaphragms (412) of diaphragm valves at side of the single-use fluidic device (420). The single-use fluidic device (420) including the valve arrangement includes a number of inlet and outlet fluid connectors (418). These fluid connectors (418) are fitted either through the clamping plate (430) for connection to external fluid processing or fluid transfer equipment or extending laterally in the plane of the plate (430) to the outside. The flow path and/or valve arrangement and the clamping device (430) include one or more positioning features (480) for aligning, engaging and securing the layers against each other. The clamping plate (430) and the valve arrangement may take up forces from liquid and pneumatic pressure. Means for mounting and/or securing any of the layers against each other and/or the system may be designed in many configurations. In certain embodiments, the means for mounting and securing the layers against each other comprise additional functions such as confirming mounting by means of an electrical feedback signal to the system or components monitoring the mounting and/or status of the flow path. In certain embodiments, the position of proximity of parts mounted against each other may trigger a feedback signal to the system or components monitoring the mounting and/or status of the flow path.

In another embodiment, it is provided a pump diaphragm system for controlling a process fluid within a liquid processing system, comprising
 a) a pump arrangement comprising at least one inlet conduit, at least one outlet conduit, and a pump diaphragm that controls the fluid flow in the conduits;
 b) a first actuator that controls the movement of the pump diaphragm;
 c) at least two check valve functionalities downstream and upstream the pump diaphragm; and
 d) a pneumatic control system comprising a pneumatic conduit interconnecting a second actuator of the pneumatic control system with the first actuator, the conduit for interconnection being intermediated by a connector unit allowing for interchanging fluid lines and/or the configuration of pneumatic conduits at side of the pump arrangement;
wherein when the pump arrangement is connected to the connector unit, one or more connections are formed, and a pump function is realized by periodically changing the pressure at the pump diaphragm. Except otherwise discussed, a pump diaphragm system is similar in design to that of the valve system described earlier, and provides similar flexibility and configurability as with the valve system described above.

In another embodiment, it is provided a system for controlling a process fluid within a liquid processing system, which system comprises a pump diaphragm sub-system according to certain embodiments of the invention combined with a valve sub-system according to certain other embodiments of the invention.

Thus, the system includes a pump diaphragm sub-system, comprising
 a) a pump arrangement comprising at least one inlet conduit, at least one outlet conduit, and a pump diaphragm that controls fluid flow in the conduits;
 b) a first actuator that controls the movement of the pump diaphragm
 c) at least two check valve functionalities downstream and upstream the pump diaphragm; and
 d) a pneumatic control system comprising first pneumatic conduits interconnecting a second actuator of the pneumatic control system with the first actuator, the conduits for interconnection being intermediated by a connector unit allowing for interchanging fluid lines and/or the configuration of pneumatic conduits at side of the pump arrangement;
wherein when the pump arrangement is connected to the connector unit, one or more connections are formed, and a pump function is realized by periodically changing the pressure at the pump diaphragm.

Thus, the system further includes a valve sub-system, comprising
 a) a valve arrangement comprising (i) a wetted part comprising two or more inlet conduits, an outlet conduit, and a plurality of valve components capable of controlling the flow in the conduits; and (ii) a plurality of third actuators that control the flow in the conduits;
 b) a pneumatic control system comprising a plurality of fourth actuators, and a plurality of second pneumatic conduits interconnecting the fourth actuators with the plurality of third actuators; and
 c) a connector unit for connecting and disconnecting at least two of the pneumatic conduits interconnecting the fourth actuators with the plurality of third actuators;
wherein when the valve arrangement is connected to the connector unit, two or more valves are formed, such that the fourth actuator controls an open/close or pressure control mode of said valves.

In certain embodiment, the pump-diaphragm sub-system and the valve sub-system share a common pneumatic control system. Thus, the second actuators and the fourth actuators are subsets of actuators within the common pneumatic control system. Further, the pneumatic conduits for the pump diaphragm sub-system and the valve sub-system are each subsets of the pneumatic conduits within the common pneumatic control system.

In certain other embodiments, the pump-diaphragm sub-system and the valve sub-system shares a common connector unit. Thus, the common connector unit may connect both the first actuators of the pump diaphragm sub-system and the third actuators of the valve arrangement, on one side, with the first and second pneumatic conduits. In certain preferred embodiments, the pump-diaphragm sub-system and the valve sub-system also share a common pneumatic control system. Thus, the pneumatic conduits for the pump diaphragm sub-system and the valve sub-system are each subsets of the pneumatic conduits within the common pneumatic control system. Further, the second actuators and the fourth actuators are subsets of actuators within the common pneumatic control system.

Now the valve arrangement and the pump arrangement are described and contrasted in some detail.

Figure 5:
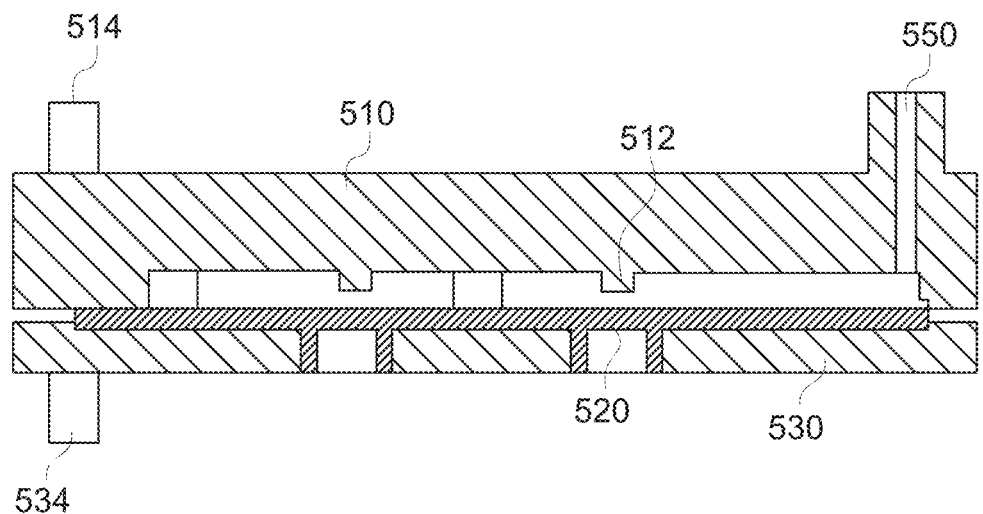
FIG. 5 shows a schematic of a cross sectional view of a valve arrangement according to certain embodiments of the invention.

FIG. 5 shows a schematic of a cross sectional view of a valve arrangement according to an embodiment of the invention. The valve arrangement comprises a valve plate (510) on one side and a valve membrane (520) supported by a plastic support plate (530) on the other side. The valve plate (510) includes a number of valve seats (512) and a number of fluid connectors (50) (one shown). The valve plate (510) optionally includes a positioning feature (514) if a clamping plate (not shown) is used. The plastic support plate (530) contains openings at locations opposite to the locations of the valve seats (512). Optionally, the plastic support plate (530) may also include a positioning feature (534).

Figure 6:
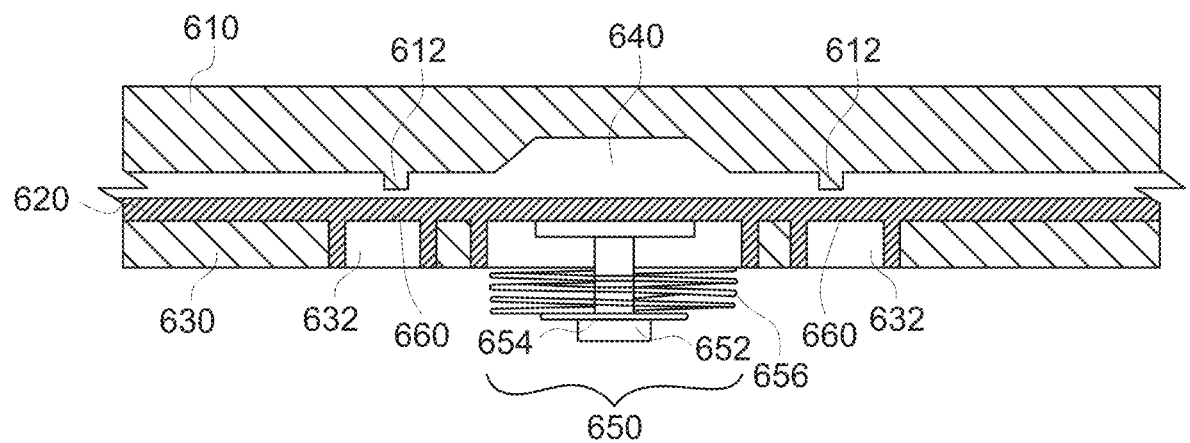
FIG. 6 shows a schematic of a cross sectional view of a pump arrangement according to certain embodiments of the invention.

FIG. 6 shows a schematic of a cross sectional view of a pump arrangement according to an embodiment of the invention. The pump arrangement comprises a pump plate (610) on one side and a membrane (620) supported by a plastic support plate (630) on the other side. The pump plate (610) includes a number of valve seats (612) and a number of fluid connectors (one shown). Alternatively, the fluid connectors and corresponding fluid lines may be integrated in a larger flow path arrangement comprising other parts and functions beyond the pump itself. The pump plate (610) optionally includes a positioning feature (not shown) if a clamping plate is used. The pump plate (610) also includes a cavity as a pump chamber (640). The plastic support plate (630) contains openings (632) at locations opposite to the locations of the valve seats (612). Optionally, the plastic support plate (630) may also include a positioning feature (not shown). The plastic support plate (630) also comprises a spring loaded pump push element (650), which includes a pump push plate (652), a clip (654) and a return spring (656). The exemplary pump shown here uses three actuators, two valves (660) defining the pumping direction and one (may be more powerful) moves the pump membrane in the middle. The pump membrane (620) is pressed in by the actuator (creating over-pressure) while the return spring moves it out (creating under-pressure) to a stop defining the stroke. Alternatively, the pump may consist of one or more actuators and at least two check valves, at least one of them is driven/controlled by the pressurized air system using the principles described here. In another embodiment, the pump may consist of at least one actuator defining the pump diaphragm and at least two check valves, at least one of the check valves not being controlled by the pneumatic system and a corresponding actuator but rather by other means, such as mechanics such as for example a spring load, by magnetic or electromagnetic field, by gravity or buoyancy or other suitable means.

Figure 7:
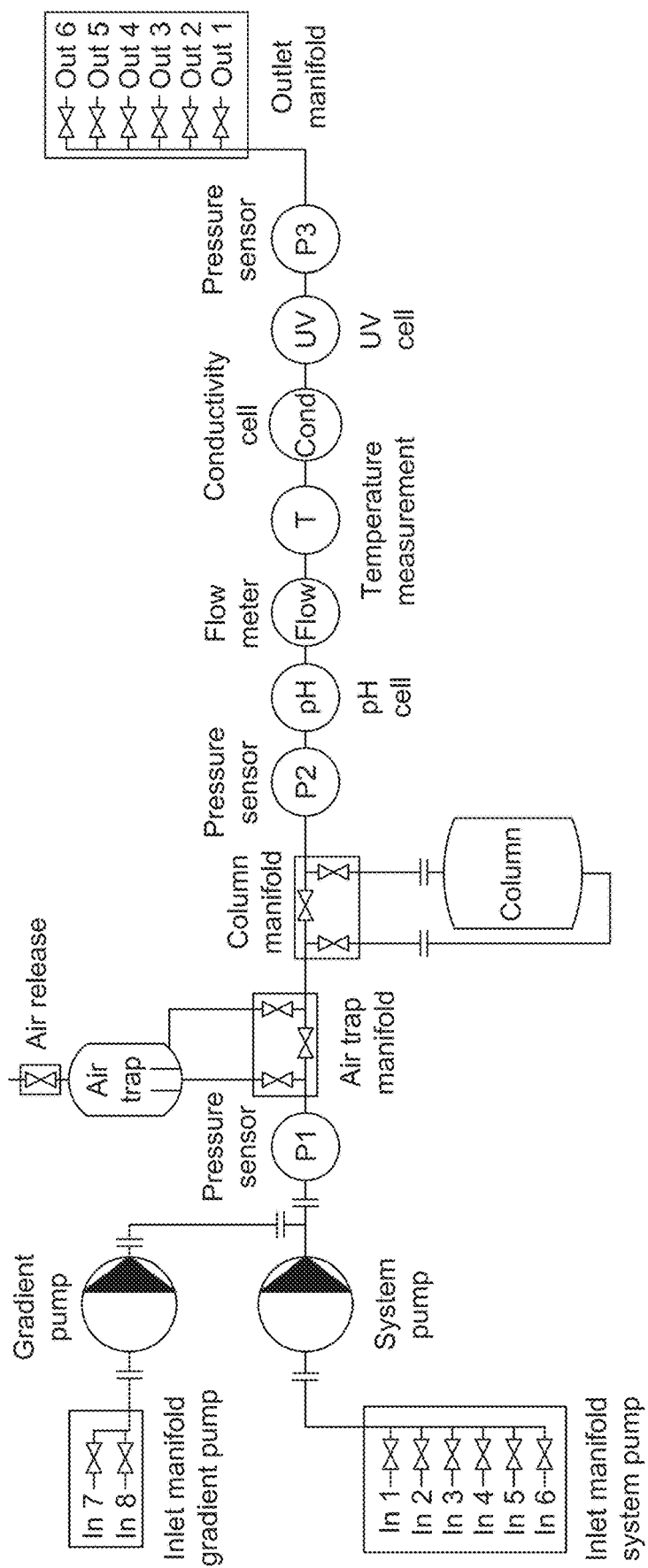
FIG. 7 shows a schematic of a flow path configuration of a liquid processing system according to certain embodiments of the invention, configured for a chromatography process.

FIG. 7 shows a schematic of a flow path configuration of a liquid processing system according to certain embodiments of the invention, configured for a chromatography process.

The example of a typical flow path for a chromatography process employs at least one inlet and one outlet valve block and manifold, respectively. The example shown also employs a second pump for formation of gradients by mixture of fluids between the two pumps, and a second inlet manifold for the gradient pump. The system may be configured for a further pump for application of sample, for example. Additional valves are used to control the liquid flow to processing components, such as a chromatography column, an air or bubble trap, a filter or a guard column (not shown). The valve arrangements can gate the liquid flow such that the component is connected in line or bypassed. Valve arrangements could be more extensive to allow liquid flow applied to the chromatography column in different directions (not shown). FIG. 7 also shows a typical arrangement of sensors for pressure, flow rate, pH, temperature, conductivity and absorbance (UV) in the liquid processing system. Similar to the chromatography column, valve arrangements could be used to connect the sensors in line or in bypass configuration (not shown). Further, valve arrangements could be configured around sensors to allow for contacting the sensors with calibration fluids using separate fluid lines not in communication with the main flow path dedicated to the process liquid (not shown).

Figure 8:
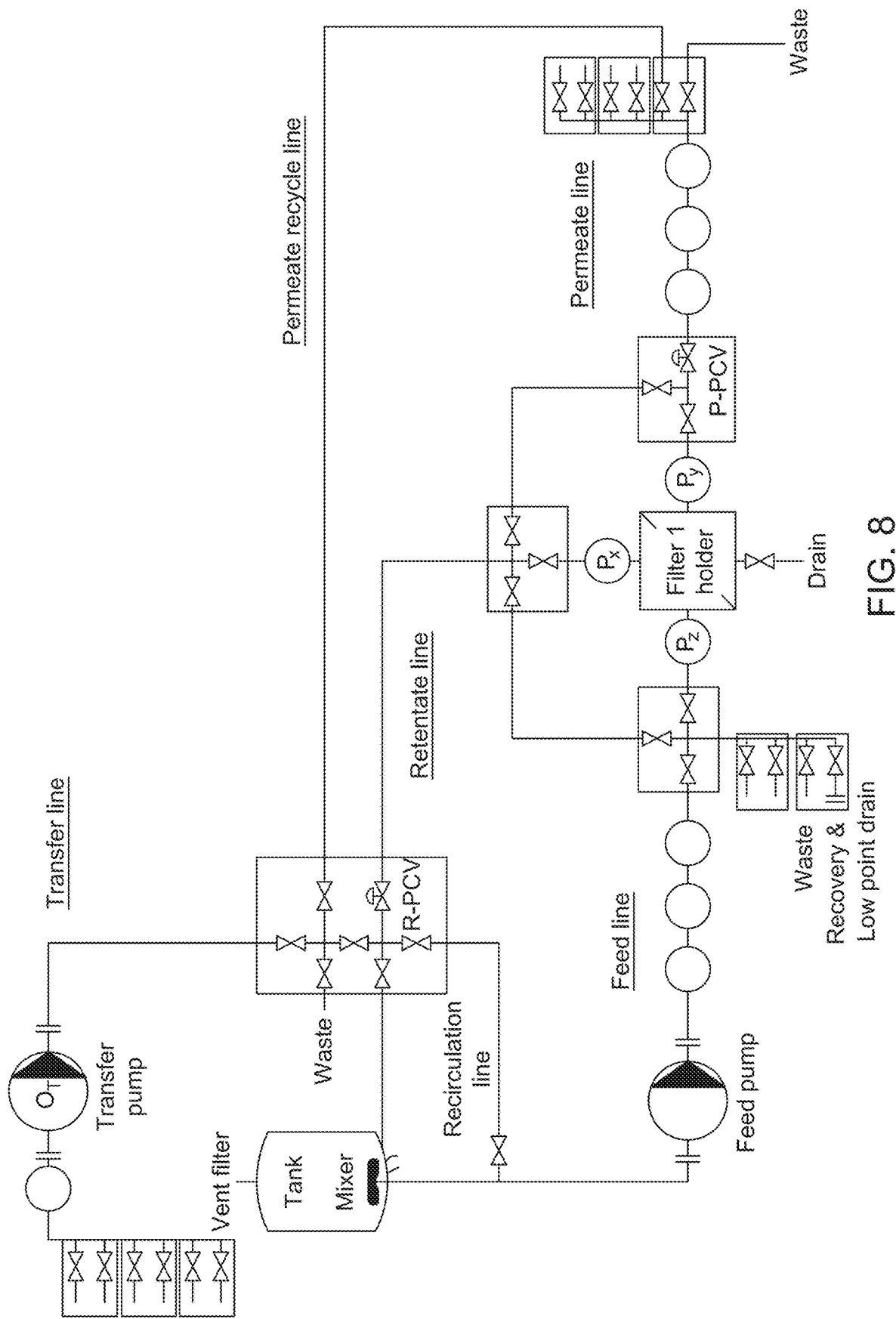
FIG. 8 shows a schematic of a flow path configuration of a liquid processing system according to certain embodiments of the invention, configured for a cross-flow filtration process.

FIG. 8 shows a schematic of a flow path configuration of a liquid processing system according to certain embodiments of the invention, configured for a cross-flow filtration process.

The example of a typical flow path for a cross-flow filtration process employs inlet and outlet valve blocks and manifolds, respectively. The process liquid is held in the tank during the cross-flow process and is recirculated over the filter unit by means of the feed pump. While process liquid is fed to the filter, filtrate or permeate passes the membrane and is removed at the filter outlet, while approximately 90% of the liquid is returned to the processing tank as 'retentate' fluid. A proportional control valve (R-PCV) is adjusted to throttle the flow of the retentate liquid and thereby adjust the retentate pressure and thus the transmembrane pressure that is the driving force for the filtration process over the filter membrane. Additional sensors measuring parameters such as conductivity, air, pH etc. are employed for process monitoring and control, although not detailed in FIG. 8. Valve blocks and manifolds are further needed and configured for bypassing processing components or for recycling the liquid flow towards the tank. The flow path configuration shown merely presents an example, however, since other configurations are possible and may be more or preferably less complex, depending on the scope of the process and the requirements for flushing, cleaning and draining the system.

Figure 9:
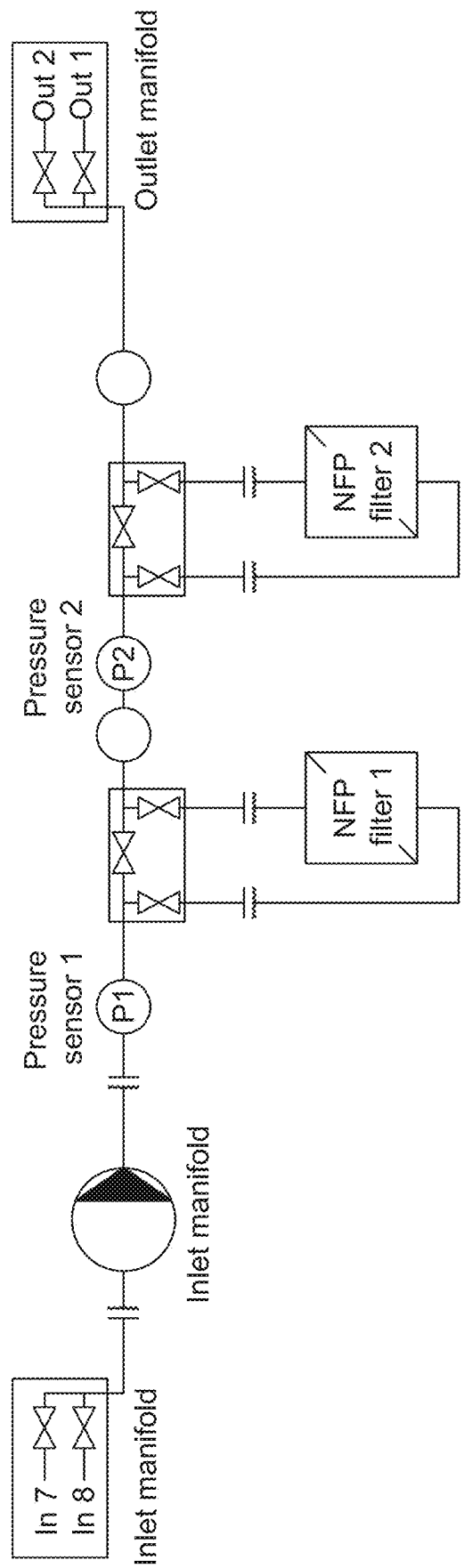
FIG. 9 shows a schematic of a flow path configuration of a liquid processing system according to certain embodiments of the invention, configured for a normal flow filtration process.

FIG. 9 shows a schematic of a flow path configuration of a liquid processing system according to certain embodiments of the invention, configured for a normal flow filtration process.

The example of a flow path for a normal flow filtration (or so-called dead end filtration) process is of lower complexity than for the examples given in FIG. 7 and FIG. 8. Typically, fewer inlets and outlets are required. Filters may be connected in series, and valve manifolds may control their connection as in line or bypass configuration.

As outlined by the examples of FIGS. 7-9, the liquid processing system and the wetted processing flow path comprising valves, pumps, sensors, filters etc. are very different depending on the processing task, here exemplified by chromatography, cross-flow filtration and normal flow filtration. Further, the individual arrangements in each processing unit may justify different configurations of for example valves with regard to number, physical arrangement, size, functionality (on/off vs. control valve). The advantage of the invention is that the pneumatic control of these valves can be managed in a cost-efficient manner by re-using the pneumatic controller and re-addressing the positions and connections of the pneumatic conduit depending on the processing needs and the installed flow path configuration. Preferably, the dimensions for the inner diameter of fluid lines in the single-use part are in the range of 0.5-50 mm, and more preferably in the range of 1-32 mm. Preferably, the dimensions of a single-use flow path layer are in the magnitude of 0.1-2.0×0.1-2.0 m, and more preferably in the magnitude of 0.2-1.5×0.2-1.5 m The liquid processing tasks and unit operations outlined above are given as examples. The invention is of course applicable to other unit operations such as Simulated Moving Bed (SMB) Chromatography, fluid mixing and fluid treatment systems. The invention shall therefore not be limited to the examples described.

Preferably, the membrane used for the valve arrangement and the pump arrangement is made from TPE (Thermo Plastic Elastomer) material.

The valve plate and pump plate may be injection molded. Preferably, they are made from JR transparent plastic weldable against TPE (SEBS, Santoprene®, etc.). The plastic support plate may be injection molded as well. Preferably, the plastic support plate is made from material suitable for over-molding with TPE (TPE IR absorbing (black)). Thus, the membrane may be laser welded to the valve plate or pump plate, while it is over-molded to the plastic support plate. The spring loaded pump-push element may be laser welded to the membrane as well.

While the particular embodiment of the present invention has been shown and described, it will be apparent to those skilled in the art that changes and modifications may be made without departing from the teachings of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. A valve system for controlling a process fluid within a liquid processing system, comprising:
    a) a valve arrangement comprising (i) a wetted part comprising two or more inlet conduits and an outlet conduit, or an inlet conduit and two or more outlet conduits, and (ii) a plurality of valve components and first actuators capable of controlling the flow in said conduits; and
    b) a pneumatic control system comprising (i) a plurality of second actuators; (ii) a plurality of pneumatic conduits interconnecting said second actuators with said plurality of first actuators; and (iii) a connector unit for connecting and disconnecting at least two of said pneumatic conduits interconnecting said second actuators with said plurality of first actuators;
    wherein when the valve arrangement is connected to the pneumatic control system, via the connector unit, the second actuators control an open/close or pressure control mode of said valves components;
    wherein the connector unit is situated on an external panel of a cabinet hosting the liquid processing system; and
    wherein the connector unit is disconnectable from the valve arrangement so as to be interchangeable with other valve units.

2. The valve system of claim 1, wherein a configuration or spatial arrangement of said valve arrangements or said connector unit may be altered to change the valve system's mode of operation.

3. The valve system of claim 1, wherein the configuration of the connector unit is altered to change the valve system's mode of operation.

4. The valve system of claim 1, wherein the configuration of the pneumatic control system is altered to change the valve system's mode of operation.

5. The valve system of claim 1, wherein the valves are diaphragm valves.

6. The valve system of claim 1, wherein the plurality of second actuators and pneumatic conduits of the pneumatic control system are situated inside the cabinet hosting the liquid processing system.

7. The valve system of claim 1, wherein the valve arrangement is a single use unit.

8. The valve system of claim 1, wherein the valve arrangement is pre-sterilized.

9. The valve system of claim 1, wherein the valve arrangement is provided as a closed and contained unit with aseptic connectors.

10. The valve system of claim 1, wherein said valve arrangement is formed by two modules, the first module comprising said wetted part and the valve components, the second module comprising said plurality of first actuators.

11. The valve system of claim 10, wherein said first and second modules are secured by a clamping device or a clamping plate.

12. The valve system of claim 10, wherein the first module is formed from a flexible pouch that is secured by a clamping device or a clamping plate.

13. The valve system of claim 1, wherein at least one of the valves is formed as a pump chamber for achieving a pump function with a substantially unidirectional displacement of liquid in at least one conduit of said liquid processing system.

14. The valve system of claim 13, wherein the valve or a displacement element of the pump is designed as a diaphragm, attached to a support structure of substantially higher rigidity.

15. The valve system of claim 14, wherein the diaphragm is attached to the support structure by laser welding, 2D injection molding or by overmolding.

16. The valve system of claim 1, wherein the valve arrangement and the connector unit each contain one or more positioning features to ensure that they are properly aligned when connected.

17. A system for purifying a biological material, the system comprising the valve system of claim 1.

* * * * *